(12) United States Patent
Barnicki et al.

(10) Patent No.: US 7,071,361 B2
(45) Date of Patent: Jul. 4, 2006

(54) PROCESSES FOR THE PREPARATION OF HIGH MOLECULAR WEIGHT SATURATED KETONES

(75) Inventors: Scott Donald Barnicki, Kingsport, TN (US); Jennifer Ellen McCusker-Orth, Kingsport, TN (US); Joseph Franklin Knight, Kingsport, TN (US); Jerry Lynn Miller, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 161 days.

(21) Appl. No.: 10/877,339

(22) Filed: Jun. 25, 2004

(65) Prior Publication Data

US 2005/0288533 A1 Dec. 29, 2005

(51) Int. Cl.
C07C 45/73 (2006.01)
(52) U.S. Cl. .................. 568/390; 568/392; 568/396
(58) Field of Classification Search ............. 568/390, 568/392, 396
See application file for complete search history.

(56) References Cited

U.S. PATENT DOCUMENTS

| | | | |
|---|---|---|---|
| 2,088,015 A | 7/1937 | Wickert | |
| 2,088,016 A | 7/1937 | Wickert | |
| 2,088,017 A | 7/1937 | Wickert et al. | |
| 2,088,018 A * | 7/1937 | Wickert et al. ............. | 260/134 |
| 2,200,216 A | 5/1940 | Loewenberg et al. | |
| 2,499,172 A | 2/1950 | Smith | |
| 2,852,563 A | 9/1958 | Hagemeyer, Jr. et al. | |
| 3,248,428 A | 4/1966 | Porter, Jr. et al. | |
| 3,670,026 A | 6/1972 | Lamparsky et al. | |
| 4,049,571 A | 9/1977 | Nissen et al. | |
| 4,101,586 A | 7/1978 | Deem et al. | |
| 4,102,930 A | 7/1978 | Deem | |
| 4,146,581 A | 3/1979 | Nissen et al. | |
| 4,270,006 A | 5/1981 | Heilen et al. | |
| 4,701,562 A | 10/1987 | Olson | |
| 4,739,122 A * | 4/1988 | Letts .......................... | 568/388 |
| 4,956,505 A | 9/1990 | Mais et al. | |
| 5,055,621 A | 10/1991 | Payne | |
| 5,243,081 A | 9/1993 | Ishino et al. | |
| 5,300,654 A | 4/1994 | Nakajima et al. | |
| 5,434,313 A | 7/1995 | Harrison et al. | |
| 5,583,263 A * | 12/1996 | Muthusamy et al. ....... | 568/396 |
| 5,663,452 A | 9/1997 | Kulmala et al. | |
| 5,840,992 A | 11/1998 | Kido et al. | |
| 5,936,131 A | 8/1999 | Teissier et al. | |
| 6,232,506 B1 | 5/2001 | Kido et al. | |
| 6,271,171 B1 | 8/2001 | Teissier et al. | |
| 6,288,288 B1 * | 9/2001 | Springer ..................... | 568/881 |
| 6,433,230 B1 * | 8/2002 | Bueschken et al. ......... | 568/388 |
| 6,583,323 B1 | 6/2003 | Krill | |
| 6,603,047 B1 | 8/2003 | Wiese et al. | |
| 2002/0058846 A1 | 5/2002 | Krill et al. | |
| 2002/0128517 A1 | 9/2002 | Krill | |
| 2002/0161264 A1 | 10/2002 | Wiese et al. | |
| 2002/0169347 A1 | 11/2002 | Kalzik et al. | |

FOREIGN PATENT DOCUMENTS

| | | |
|---|---|---|
| EP | 0 141 569 A2 | 5/1985 |
| GB | 446026 | 4/1936 |
| GB | 549066 | 11/1942 |
| GB | 1010695 | 11/1965 |
| WO | WO 02/24621 A1 | 3/2002 |

OTHER PUBLICATIONS

Weizmann and Garrard, "Some Condensations of N-butyl Alcohol and N-butaldehyde", *J. Chem. Soc. Trans.*, vol. 117, 1920, pp. 324-338.
M. Lakshmi Kantam et al, "Aldol and Knoevenagel condensations catalysed by modified Mg-Al hydrotalcite:a solid base as catalyst useful in synthetic organic chemistry" *Chem. Comm.*, 1998, pp. 1033-1034.
PCT International Search Report and Written Opinion for PCT/US2004/020489.
U.S. Appl. No. 10/611,394, filed Jul. 1, 2003.
U.S. Appl. No. 10/713,727, filed Nov. 14, 2003.
Weizmann and Garrard, J. Chem., Soc., Pt. 1, vol. 117, 1920 pp. 324-338.
Eccott and Linstead, J. Chem. Soc., Pt. 1, vol. 133, pp. 905-911.
Kyrides, Journal of the Amer. Chem. Soc., vol. 55, Aug. 1933, pp. 3431-3435.
Powell, Journal of the Amer. Chem. Soc., vol. 46, 1924, pp. 2514-2517.
Streitwiser and Heathcock, "Introduction to Organic Chemistry", 2d Ed., 1981, pp. 392-396.

(Continued)

Primary Examiner—Johann Richter
Assistant Examiner—Sikarl A. Witherspoon
(74) Attorney, Agent, or Firm—Polly C. Owen; Bernard J. Graves, Jr.

(57) ABSTRACT

Continuous single-step processes for producing higher molecular weight ketones are disclosed that involve a liquid-phase crossed condensation of an aldehyde with a ketone in the presence of a hydrogenation catalyst and a small amount of a catalyst comprising a concentrated hydroxide or alkoxide of an alkali-metal (from Group 1 or Group IA of the Periodic Table of the Elements) or alkali-earth metal (from Group 2, or Group IIA of the Periodic Table of the Elements), wherein the amount of water provided to the reaction mixture, or reaction zone, is relatively low, with respect to the total initial weight of the reaction mixture. The reaction may be carried out in the absence of solubilizing agents or phase transfer agents. The product mixture is largely free of by-products resulting from further condensation reactions of the desired ketone product or intermediates, and free of the self-condensation products of the reactant aldehyde, that are afterward difficult to remove from the reaction mixture.

34 Claims, No Drawings

OTHER PUBLICATIONS

H. O. House, Modern Synthetic Reactions, 2d Ed., 1972, pp. 595-599, 629-640.

Period Table of the Elements, as published in "Chemical and Engineering News", 63(5), 27, 1985.

Roger Adams et al., Organic Reactions, vol. 2, 1944, pp. 94-113.

Grignard and Dubien, Action of Organomagnesium Compounds on Butylidence-Acetone and its Ketol, Ann. De Chim., 10$^{th}$ serier, 2:282-290, Nov.-Dec. 1924.

Office Action mailed Jun. 15, 2004 in U.S. Appl. No. 10/611,394.

* cited by examiner

PROCESSES FOR THE PREPARATION OF HIGH MOLECULAR WEIGHT SATURATED KETONES

FIELD OF THE INVENTION

This invention relates to processes for producing ketones, and more specifically, to processes for producing higher molecular weight saturated ketones that result in higher yields, higher space-time yields, and greater selectivity for the target product, while minimizing the formation of by-products.

BACKGROUND OF THE INVENTION

Aldol condensation reactions are important in the production of intermediates needed to synthesize many commercially important products. The condensation of ketones to obtain aldols (β-hydroxy ketones) is a well-known reaction. Dehydration of the resulting aldol to obtain an unsaturated ketone is also known. Subsequent catalytic hydrogenation of the unsaturated ketone may be carried out to obtain the corresponding saturated higher ketone.

In an aldol condensation reaction, an aldehyde or ketone, with a hydrogen atom alpha to the carbonyl, react together to form a β-hydroxy-aldehyde or a β-hydroxy-ketone. The β-hydroxy-aldehyde or β-hydroxy-ketone can dehydrate in the presence of either an acid or a base to give a conjugated α,β-unsaturated aldehyde or ketone. The conditions needed for the aldol dehydration are often only slightly more vigorous than the conditions needed for the aldol condensation itself. As a result, the product of such aldol reactions often comprises both the β-hydroxy aldehyde or ketone and the α,β-unsaturated aldehyde or ketone.

Many methods have been disclosed in the art to perform aldol condensation reactions. These include two-phase liquid reactions using dilute aqueous base as the catalyst, see, for example, U.S. Pat. No. 6,232,506, U.S. Pat. Appln. No. 2002/0161264, U.S. Pat. No. 6,433,230, U.S. Pat. No. 2,200,216, U.S. Pat. No. 6,288,288; base-catalyzed, liquid phase aldol condensation reactions that include the use of a solubilizing or phase transfer agent, see, for example, U.S. Pat. Nos. 2,088,015, 2,088,016, 2,088,017, and 2,088,018; and the use of polymeric or oligomeric ethylene glycols or polyhydric alcohols as phase transfer catalysts or solvents in combination with dilute alkali metal hydroxide catalysts, see, for example, U.S. Pat. Nos. 5,055,621, and 5,663,452, and U.S. Pat. Publ. No. 2002/0058846.

Several authors have disclosed processes for crossed aldol condensations catalyzed by relatively high levels of caustic. Weizmann and Garrard, J. Chem. Soc, Pt. 1, Vol. 117, 1920, pp. 324–338, prepared 3-hepten-2-one by the batch-wise crossed condensation of n-butyraldehyde and acetone catalyzed with solid sodium hydroxide. Eccott and Linstead, J. Chem. Soc, Pt. 1, Vol. 133, 1930, pp. 904–911, prepared a mixture of 4-hydroxy-2-heptanone and 3-hepten-2-one by the low-temperature, (5–10° C.) batch-wise crossed condensation of n-butyraldehyde and acetone catalyzed by 50 weight percent sodium hydroxide. As another example, U.S. patent application Ser. No. 10/611,394, filed Jul. 1, 2003 and having common assignee herewith, describes a process for the preparation of β-hydroxy-ketones and/or α,β-unsaturated ketones in unexpectedly high yields by the liquid-phase crossed condensation of an aldehyde with a ketone, in the presence of a small amount of a catalyst comprising a concentrated hydroxide or alkoxide of an alkali-metal or alkali-earth metal, wherein the amount of water present in the reaction mixture is kept relatively low, with respect to the total weight of reactants.

The β-hydroxy-aldehyde or β-hydroxy-ketone product of such aldol condensations can dehydrate to give a conjugated α,β-unsaturated aldehyde or ketone. Many methods are known in the art for dehydrating β-hydroxy-aldehydes or β-hydroxy-ketones to α,β-unsaturated aldehydes or ketones, in fair to excellent yields. These include simple heating; acid-catalyzed dehydration using mineral acids or solid acid catalysts, with or without azeotropic removal of the water of reaction, as exemplified in U.S. Pat. No. 5,583,263, U.S. Pat. No. 5,840,992, U.S. Pat. No. 5,300,654, and Kyrides, JACS, Vol 55, August, 1933, pp. 3431–3435; heating with iodine crystals, as in Powell, JACS, Vol. 46, 1924, pp. 2514–17; and base-catalyzed dehydration, as taught in Streitwieser and Heathcock, "Introduction to Organic Chemistry", $2^{nd}$ Ed., 1981, pp. 392–396.

Aldehydes are more reactive, in general, than are ketones in base-catalyzed aldol condensations, because of the greater ease of enolate ion formation of an aldehyde. As such, in a crossed condensation of a ketone with an aldehyde to produce a desired β-hydroxyketone, the self-condensation of the aldehyde typically occurs in substantial quantities to produce an undesired β-hydroxyaldehyde by-product. Further, unhindered aldehydes, i.e., straight-chain aldehydes such as acetaldehyde, propionaldehyde, n-butyraldehyde, and n-pentanal, are more reactive toward self-condensation than are hindered aldehydes, i.e., branched aldehydes such as 2-methyl-propanal and 3-methyl-butanal.

It is understood that the rate-limiting step in these reactions is often the enolate ion formation, and that condensation and the subsequent dehydration reaction occur in rapid succession. These α-β unsaturated ketones and aldehydes are known to those skilled in the art to be quite reactive and susceptible to further consecutive, non-selective condensation, cyclization, and Michael-type addition reactions with the starting ketones and aldehydes, as well as themselves and other ketonic and aldehydic by-products. See, for example, H. O. House, Modern Synthetic Reactions, $2^{nd}$. Ed., 1972 pp. 595–599, 629–640.

Thus, without being bound by any theory, in the base-catalyzed condensation of an aldehyde of Formula 1, possessing at least one hydrogen atom alpha to the carbonyl, with a ketone of Formula II, to form a desired β-hydroxy-ketone or α-β unsaturated ketone of Formulae III or IV, three parallel reaction pathways are known to compete:

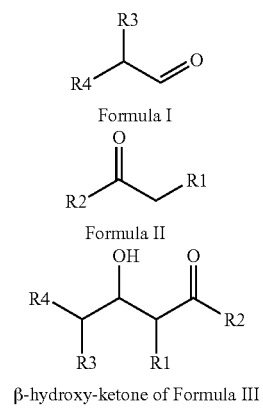

β-hydroxy-ketone of Formula III

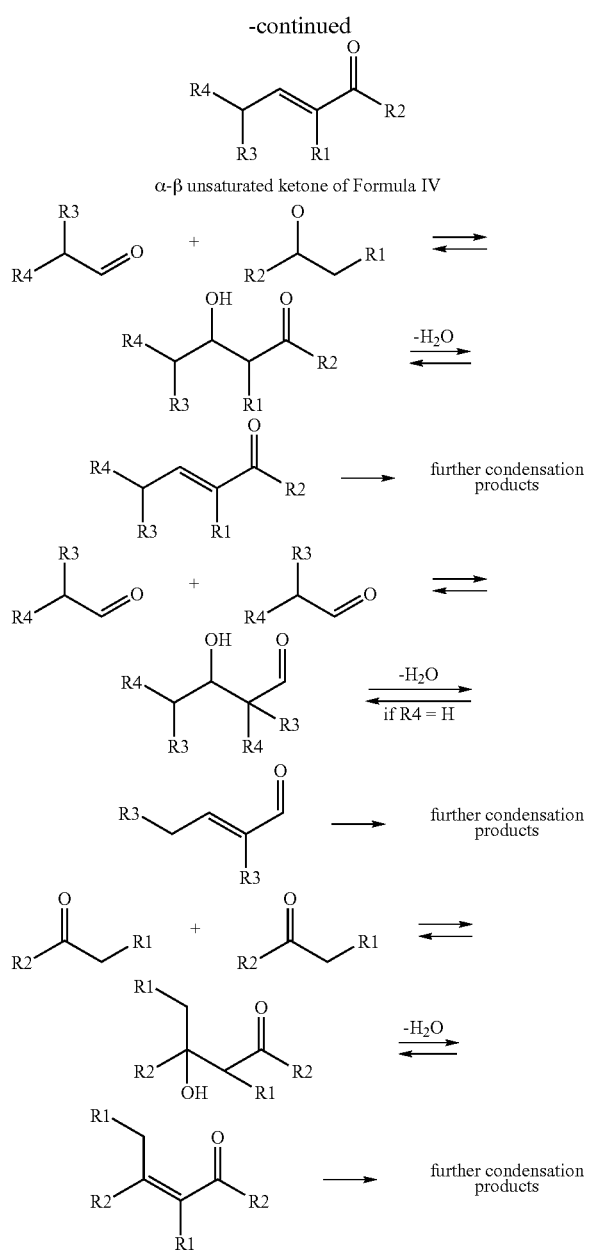

In general, R2 represents a C1 to C10 organic radical and R1, R3, and R4 represent hydrogen or a C1 to C10 organic radical.

R1 may represent a hydrogen, or else R1 and R2 may form members of a common cycloalkyl or aromatic ring, either of which may be substituted with one or more functional groups, or else R2 represents an alkyl group, which may be straight or branched, and which may be substituted with one or more functional groups;

R3 and R4 each independently represent hydrogen, or else R3 and R4 form members of a common cycloalkyl or aromatic ring, either of which may be substituted with one or more functional groups, or else one or both may represent a branched or unbranched, saturated or unsaturated aliphatic or alkyl-substituted cycloalkyl hydrocarbon radical; or else each represents an aryl hydrocarbon radical, or an alkylaryl hydrocarbon radical, either of which may be substituted with one or more functional groups.

One skilled in the art would expect a broad range of products from these reactions, and difficulty in stopping the reactions at the β-hydroxy-ketone stage. The further condensation of the α-β unsaturated ketones with the ketone of Formula II, or with the aldehyde of Formula I, or with other ketonic and aldehydic species, leads to a plethora of by-products and can represent significant yield losses as well as necessitating complicated and expensive purification schemes for the commercial production of high purity β-hydroxy-ketones and/or α,β-unsaturated ketones. For example, in the preparation of 2-heptanone via the condensation of n-butyraldehyde with acetone, the self-condensation of n-butyraldehyde to form 2-ethyl-2-hexenal is a particularly troublesome by-product. Its hydrogenated form, 2-ethylhexanal, boils less than 10° C. apart from 2-heptanone, and is therefore difficult to separate economically from 2-heptanone by distillation.

One method of preventing unwanted further condensation side products in aldol condensation reactions is to quickly hydrogenate the α,β-unsaturated ketones. This can be accomplished in situ or in a separate hydrogenation step.

In some cases, it is desirable to selectively hydrogenate the carbon—carbon double bond of the resulting α,β-unsaturated ketone to give a saturated ketone. Catalysts and methods are known for such hydrogenation reactions, as exemplified in U.S. Pat. Nos. 5,583,263 and 5,840,992, and U.S. Pat. Appl. Nos., 2002/0128517, 2002/058846, and 2002/0169347. Alkenes react with hydrogen gas in the presence of a suitable metal catalyst, typically palladium or platinum, to yield the corresponding saturated alkane addition products. The metal catalysts are normally employed on a support or inert material, such as carbon or alumina. Commercially important products of this type include methyl amyl ketone, methyl isoamyl ketone, and methyl propyl ketone, made by the crossed condensation of acetone with n-butyraldehyde, isobutyraldehyde, or acetaldehyde, respectively.

The production of higher molecular weight ketones using aldol condensations and catalytic hydrogenations can be carried out either by a multi-step process or a single-step process. A multi-step process uses sequentially discrete steps in two or three separate reactors. In a single-step process the reactions are carried out simultaneously in one reactor.

When ketones are synthesized by a multi-step process, using sequentially discrete steps, the aldol reaction occurs first, which is then followed by dehydration, and by subsequent hydrogenation. Each step is independent of the others, and the process often requires difficult separation techniques between steps. For example, U.S. Pat. No. 5,583,263 describes a multi-step process for the coproduction of methyl amyl ketone and methyl isobutyl ketone. In this process, dimethyl ketone is reacted with n-butyraldehyde using a fixed-bed basic ion exchange cross-aldol condensation catalyst to form a β-hydroxy ketone mixture. The product is then dehydrated to form an olefinic ketone using a catalytic quantity of an acidic substance, such as $H_2SO_4$, $NaHSO_4$, or a sulfonic acid resin. The resulting α,β-unsaturated ketone is then hydrogenated using a solid phase hydrogenation catalyst to produce the desired amyl ketone. Three discrete steps are required, with costly separations between the steps. There is no acknowledgment that by-products other than methyl isobutyl ketone are produced, nor is there any suggestion how one might avoid impurities such as 2-ethylhexaldehyde and high boiling by-products that result from unwanted side reactions. On the basis of a comparative example, the authors conclude that commercial coproduction of methyl isobutyl ketone and methyl amyl ketone is impractical in one-step processes employing ordinary catalyst systems.

Another example of a multi-step process is found in U.S. Pat. No. 5,840,992 ('992), which teaches a process for producing 6-methylheptan-2-one by the crossed condensation of acetone with 3-methyl-butanal, in the presence of an aqueous alkali or alkali earth metal hydroxide as catalyst, at a catalyst-aldehyde molar ratio of 0.001 to 0.20. In a separate step, the resulting β-hydroxy ketone condensation product is further subjected to reduction under dehydrating conditions to produce 6-methylheptan-2-one. The process according to the '992 patent may be carried out continuously in plug flow or batch-wise mode. Typical molar selectivities on 3-methyl-butanal are about 75 to 80 percent, with the best results being achieved in the batch mode of operation. Although the '992 patent suggests that the basic catalyst substance may be used as an aqueous solution at a concentration between 1 and 50 percent, the process is reduced to practice only with a catalyst concentration of 5 weight percent aqueous sodium or potassium hydroxide. The authors of the '992 patent clearly fail to contemplate the advantages of using concentrated hydroxides or alkoxides of alkali earth- or alkali-metals as catalysts, for example at greater than 15 or 20 weight percent, while controlling the absolute amount of water present in the reaction mixture. Thus, the process disclosed in the '992 patent achieves only modest yields.

U.S. Pat. No. 6,232,506 discloses a multi-step process for producing 6-methyl-3-heptan-2-one, and its analogues, by the crossed aldol condensation of acetone with 3-methylbutanal (isovaleraldehyde), in the presence of an aqueous alkali containing an alkaline substance. The 6-methyl-3-hepten-2-one is then separately hydrogenated to 6-methyl-3-heptan-2-one in the presence of a hydrogenation catalyst. The aldol catalyst is provided as a 0.5 to 30 weight percent, preferably 1 to 10 weight percent, aqueous solution, at a caustic-aldehyde molar ratio of 0.001 to 0.2. The process is carried out in semi-batch mode, with separate continuous feeds of aldehyde and dilute caustic to a stirred reaction zone initially comprising acetone. In Example 3 of the patent, using the preferred 2 wt. % aqueous caustic catalyst solution, the reaction mixture forms distinct aqueous and organic phases, with water being present in an amount of about 39 wt. %, based on the total weight of the reactant mixture. 6-methyl-3-hepten-2-one is hydrogenated in the presence a 5% palladium on carbon catalyst for 7 hours. Cited yields are typically about 66% to 6-methyl-3-hepten-2-one and 3.3% 6-methyl-4-hydroxy-heptan-2-one.

U.S. Pat. No. 6,603,047 discloses a step-wise process for the preparation of ketones by the crossed condensation of an aldehyde with a ketone, followed by the hydrogenation of the unsaturated ketone. The condensation reaction described can be carried out in a tubular reactor as a multiphase liquid reaction in which a dilute aqueous caustic catalyst (0.1 to 15 weight percent caustic, preferably 0.1 to 5 weight percent) is the continuous phase and the aldehyde/ketone reactants are the dispersed phase. This patent explains that the reaction must be conducted with separate catalyst and reactant phases, and that the mass ratio of the aqueous caustic phase to the organic reactant phase can be from 2:1 to 10:1, preferably even greater. The reference clearly fails to contemplate the advantages of a high caustic catalyst phase reaction in which the amount of water present is kept relatively low. The patent claims the unsaturated ketone is hydrogenated in a separate step, but this concept is not reduced to practice in the examples.

When ketones are produced in a single-step process, the aldol reaction, dehydration, and hydrogenation occur simultaneously in one reactor. Such single-step processes can be either batch or continous processes.

In a single-step batch process, the reactions are carried out simultaneously in one reactor, and there is neither inflow nor outflow of reactants or products while the reaction is being carried out. In a one-step continuous process, the reactions are carried out simultaneously in one reactor, and reactants flow in and the products flow out while the reaction is being carried out. While the hydrogenation reaction is typically heterogeneously catalyzed, the aldol condenstion can be either heterogeneously or homogeneously catalyzed in a one-step process.

For example, U.S. Pat. No. 2,499,172 (the '172 patent) describes a single-step batch process for the conversion of low-boiling ketones to high boiling ketones. Higher boiling ketones, such as methyl isobutyl ketone, are produced when lower boiling ketones, such as acetone and ethyl methyl ketone, are treated with hydrogen in the presence of a liquid alkaline condensation catalyst and a solid hydrogenation catalyst. The liquid alkaline condensation catalyst can be ammonia; amines, such as isopropylamine, diisopropylamine, trimethylamine, furfurylamine, difurfurylamine, and aniline; alkali-metal hydroxides; alkaline-earth-metal oxides and hydroxides; and alkali-metal salts of weak acids, such as sodium borate, carbonate, acetate and phosphates. The solid hydrogenation catalyst can contain palladium, for example 5% Pd/C.

The examples of the '172 patent describe a single-step batch process for the self-condensation of ketones. In general, self-aldol condensations of ketones lead to only one product. For example, the self-aldol condensation and hydrogenation product of dimethylketone is methyl isobutyl ketone. However, crossed aldol condensations—between ketones and aldehydes—lead to mixtures of products. For example, the crossed aldol condensation and hydrogenaton products of dimethylketone and n-butyraldehyde are methyl amyl ketone, methyl isobutyl ketone, and 2-ethylhexaldehyde. We have found that when the one-step batch process described in the '172 patent is applied to the crossed aldol condensation of acetone and n-butyraldehdye, as seen in Example 1 (Comparative) of the present application, a large amount of high-boiling material is produced. As a result, the selectivity of n-butyraldehyde to methyl amyl ketone is poor. A further disadvantage of batch processes in general is that they often require large reaction vessels and storage tanks, because their productive capacity relative to the reaction volume is very small. Other drawbacks include high energy consumption and high labor requirements.

U.S. Pat. No. 6,583,323 describes a single-step process for the preparation of 6-methylheptan-2-one and corresponding homologous β-branched methylketones, in particular phytone and tetrahydrogeranyl acetone, by the two-liquid phase crossed condensation of acetone with 3-methyl-butanal, prenal or the like, in the presence of both a dilute aqueous alkali or alkali earth metal hydroxide catalyst for the aldol step and a noble metal catalyst for hydrogenation. A base concentration of 0.01 to 20 weight percent in the aqueous catalyst phase is said to be useful, from 0.5 to 5 wt. % being preferred, though the concentration is said not to be critical. The processes exemplified in this document use relatively low concentrations of caustic with a relatively high amount of water, with respect to the total weight of the reactants. The reactivity toward self-condensation of the hindered, branched aldehyde, 3-methyl-butanal, is low, resulting in molar selectivities based on the aldehyde of around 93–95 mole percent.

U.S. Pat. Publ. No. 2002/0058846 teaches a single-step process for the preparation of 6-methylheptan-2-one and corresponding homologous β-branched methylketones, in particular phytone and tetrathydrogeranyl acetone, by the two-liquid phase crossed condensation of acetone with 3-methyl-butanal, prenal or the like, in the presence of a dilute aqueous alkali or alkali earth metal hydroxide catalyst dissolved in a polyhydric alcohol for the aldol step, and a noble metal catalyst for hydrogenation. The polyhydric alcohol is preferably glycerol. This process suffers from low reaction rates and complicated separation schemes for recovery and recycling of the phase transfer catalyst.

U.S. patent application Ser. No. 10/713,727, filed Nov. 14, 2003 and having common assignee herewith, describes a single-step process for producing higher molecular weight ketones, which occurs in a fixed-bed reactor system. Aliphatic ketones or aldehydes are condensed together using a dilute liquid base as an aldol catalyst. The resulting intermediate is dehydrated by the liquid base to yield an unsaturated intermediate. This olefinic species is then hydrogenated over a solid metal catalyst on an inert support. While high conversions and good selectivity are achieved with this process, high recycle rates are suggested for low by-product formation. There remains a need for an improved process for producing higher molecular weight ketones having a higher yield and greater selectivity for the target product, which minimizes the amounts of unwanted by-products that are afterward difficult to remove from the reaction mixture.

BRIEF SUMMARY OF THE INVENTION

We have discovered that higher molecular weight ketones may be produced with high yields, and high space-time yields, in a continuous single-step process by the liquid-phase crossed condensation of an aldehyde with a ketone in the presence of a hydrogenation catalyst and a small amount of a catalyst comprising a concentrated hydroxide or alkoxide of an alkali-metal (from Group 1 or Group IA of the Periodic Table of the Elements) or alkali-earth metal (from Group 2, or Group IIA of the Periodic Table of the Elements), wherein the amount of water provided to the reaction mixture, or reaction zone, is relatively low, with respect to the total weight of the reaction mixture. The reaction may be carried out in the absence of solubilizing agents or phase transfer agents. The product mixture is largely free of by-products resulting from further condensation reactions of the desired ketone product or intermediates, and free of the self-condensation products of the reactant aldehyde that are afterward difficult to remove from the reaction mixture.

DETAILED DESCRIPTION OF THE INVENTION

The present invention may be understood more readily by reference to the following detailed description of the invention, and to the Examples included therein.

Before the present compositions of matter and methods are disclosed and described, it is to be understood that this invention is not limited to specific synthetic methods or to particular formulations, unless otherwise indicated, and, as such, may vary from the disclosure. It is also to be understood that the terminology used is for the purpose of describing particular embodiments only, and is not intended to limit the scope of the invention.

The singular forms "a," "an," and "the" include plural referents, unless the context clearly dictates otherwise.

Optional or optionally means that the subsequently described event or circumstances may or may not occur. The description includes instances where the event or circumstance occurs, and instances where it does not occur.

Ranges may be expressed herein as from about one particular value, and/or to about another particular value. When such a range is expressed, it is to be understood that another embodiment is from the one particular value and/or to the other particular value.

Throughout this application, where patents or publications are referenced, the disclosures of these references in their entireties are intended to be incorporated by reference into this application, in order to more fully describe the state of the art to which the invention pertains.

By the term "higher" molecular weight ketones, as used herein, we mean that the molecular weights of the ketone products are higher than are the molecular weights of the reactants. Conversely, by the terms "lower" molecular weight ketones and "lower" molecular weight aldehydes, as used herein, we mean that the molecular weights of these reactants are lower than the molecular weights of the resulting ketone products.

All mention herein to elements of Groups of the Periodic Table, unless the context indicates otherwise, are made in reference to the Periodic Table of the Elements, as published in "Chemical and Engineering News", 63(5), 27, 1985. In this reference, the groups are numbered 1 to 18.

New processes have been found for producing higher molecular weight ketones, having a combination of product selectivity and space-time yield heretofore unrecognized in the art.

According to one embodiment of the invention, a higher molecular weight saturated ketone of Formula V is produced by the liquid-phase crossed condensation of an aldehyde reactant of Formula I with a ketone reactant of Formula II.

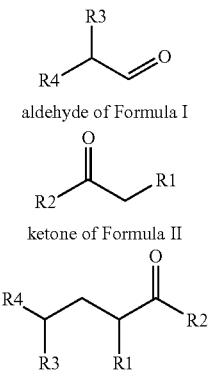

aldehyde of Formula I ketone of Formula II higher molecular weight ketone of Formula V The aforementioned crossed condensation is carried out in the presence of a heterogeneous (solid) hydrogenation catalyst, typically a metal catalyst, wherein the transition metal is typically supported on an inert stable support. Further, the condensation is carried out in the presence of a small amount of an aldol catalyst comprising one or more bases, and especially a concentrated hydroxide or alkoxide of an alkali- or alkali-earth metal, wherein the amount of water provided to the reaction mixture, or the reaction zone, is relatively low, in certain embodiments being no more than about 16 wt. %, with respect to the total weight of the reactant mixture. In other embodiments, the amount of water provided to the reaction mixture, or the reaction zone, may be no more than about 12 wt. %, with respect to the total weight of the reactant mixture, or no more than 5 wt. %, or no more than 3 wt. %, or even 1 wt. % or less, with respect to the total initial weight of the reaction mixture.

In one embodiment, R1 represents hydrogen, or else R1 and R2 form members of a common alicyclic ring of 4 to 12 carbon atoms, preferably 4 to 8 carbon atoms, and especially 5 to 6 carbon atoms, which alicyclic ring may be substituted with one or more branched or unbranched, saturated or unsaturated aliphatic or alkyl-substituted cycloaliphatic, or aromatic hydrocarbon radicals of 1 to 20 carbon atoms, preferably 1 to 12 carbon atoms, or with halogens, ethers, thio ethers, or amine functionalities; or else R2 represents a branched or unbranched, saturated or unsaturated aliphatic or alkyl-substituted cycloaliphatic hydrocarbon radical of 1 to 20 carbon atoms, preferably from 1 to 12 carbon atoms, or from 1 to 4 carbon atoms, and especially a methyl, ethyl, n-butyl, t-butyl, or i-butyl radical, which aliphatic or alkyl-substituted cycloaliphatic hydrocarbon radical may be substituted with halogens or ether functionalities; or else R2 represents a saturated or unsaturated alkyl-substituted cycloaliphatic hydrocarbon radical of 3 to 12 carbon atoms, preferably 3 to 8 carbon atoms, and especially 5 to 6 carbon atoms, which cycloaliphatic hydrocarbon radical may contain alkyl groups as substituents, and which may be substituted with halogens or ether functionalities; or else R2 represents an aryl hydrocarbon radical of 6 to 15 carbon atoms, preferably 6 to 9 carbon atoms, and especially a phenyl radical, which aryl hydrocarbon radical may be substituted with halogens or ether functionalities; or else R2 represents an alkylaryl hydrocarbon radical of 7 to 15 carbon atoms, preferably 7 to 10 carbon atoms, and especially a benzyl radical, which alkylaryl hydrocarbon radical may be substituted with halogens or ether functionalities;

R3, and R4 may each independently represent hydrogen, or else R3 and R4 form members of a common alicyclic ring of 4 to 12 carbon atoms, preferably from 4 to 8 carbon atoms, and especially 5 to 6 carbon atoms, such as a cyclohexyl radical, which alicyclic ring may be substituted with one or more branched or unbranched, saturated or unsaturated aliphatic or alkyl-substituted cycloaliphatic, or aromatic hydrocarbon radicals of 1 to 20 carbon atoms, preferably 1 to 12 carbon atoms, or with halogens or ether functionalities; or else R3 or R4 may represent a branched or unbranched, saturated or unsaturated aliphatic or alkyl-substituted cycloaliphatic hydrocarbon radical of 1 to 20 carbon atoms, preferably from 1 to 12 carbon atoms, and especially from 1 to 6 carbon atoms, such as a methyl, ethyl, n-propyl, or n-butyl radical, which aliphatic or cycloaliphatic hydrocarbon radical may be substituted with halogens or ether functionalities; or R3 or R4 may represent a saturated or unsaturated alkyl-substituted cycloaliphatic hydrocarbon radical of 3 to 12 carbon atoms, preferably from 3 to 8 carbon atoms, and especially from 5 to 6 carbon atoms, which cycloaliphatic hydrocarbon radical may contain alkyl groups as substituents, or which may be substituted with halogens or ether functionalities; or else R3 or R4 may represent an aryl hydrocarbon radical of 6 to 15 carbon atoms, preferably from 6 to 9 carbon atoms, and especially a phenyl radical, which aryl hydrocarbon radical may be substituted with halogens or ether functionalities; or else R3 or R4 may represent an alkylaryl hydrocarbon radical of 7 to 15 carbon atoms, preferably from 7 to 10 carbon atoms, and especially a benzyl radical, which alkylaryl hydrocarbon radical may be substituted with halogens or ether functionalities.

In a similar embodiment, R1, R3, and R4 each represent hydrogen, or R1, R2, R3, and R4 each represent a substituted or unsubstituted, straight or branched chain aliphatic radical containing 1 to 10 carbon atoms; a substituted or unsubstituted, straight or branched chain alkenyl radical containing 2 to 10 carbon atoms; a substituted or unsubstituted cycloalkyl or cycloalkenyl radical containing 4 to 10 carbon atoms; a substituted or unsubstituted aryl radical containing 6 to 10 carbon atoms, e.g., phenyl or napthyl; or a substituted or unsubstituted 4- to 10-membered heterocylic radical containing from 1 to 3 heteroatoms selected from oxygen and sulfur. The term "heterocyclic radical" denotes optionally substituted four to ten-membered rings that have 1 to 3 heteroatoms, selected independently from oxygen and sulfur. These four- to ten-membered rings may be saturated, partially unsaturated, or fully unsaturated.

The term "substituted" as used herein in conjunction with each of the above alkyl, alkenyl, cycloalkyl, cycloalkenyl, aryl, and heterocyclic radicals which may be represented by R1, R2, R3, and R4 denotes the above radicals substituted with one or more halogen, $C_1$–$C_6$-alkyl, $C_1$–$C_6$-alkoxy, substituted $C_1$–$C_6$-alkyl, $C_1$–$C_6$-alkylthio, aryl, arylthio, aryloxy, $C_2$–$C_6$-alkoxycarbonyl, $C_2$–$C_6$-alkanoylamino, hydroxy, carboxyl, cycloalkoxy, nitro, keto, thioether, aldehydo, carboalkoxy, imido, sulfinato, sulfanato, sulfonamide, sulfoxy, phosphato, cycloalkyl, amino, mono-substituted amino, di-substituted amino, acyloxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkoxy, acyloxy, acyl, alkyl, alkoxy, aminoacyl, acylamino, azido, carboxylalkyl, cyano, heteroaryl, heteroaryloxy, heterocyclyl, heterocyclooxy, aminoacyloxy, oxyacylamino, thioalkoxy, substituted thioalkoxy, thioaryloxy, thioheteroaryloxy, trihalomethyl, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, or arylcarbonylamino groups.

Examples of substituted and unsubstituted alkyl and alkenyl radicals include, but are not limited to, methyl, ethyl, cyanomethyl, nitromethyl, hydroxymethyl, trityloxymethyl, propionyloxymethyl, aminomethyl, carboxymethyl, allyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(iso-propyl), 2-carbamoyloxyethyl, n-propyl, isopropyl, isobutyl, n-butyl, tertiary butyl, pentyl, hexyl, 2-ethylhexyl, octyl, decyl, vinyl, 1-propenyl, 1-butenyl, 1-pentenyl, 2-octenyl, and various isomers thereof.

Examples of substituted and unsubstituted cycloalkyl and cycloalkenyl radicals include, but are not limited to, cyclopropyl, cyclobutyl, hydroxymethylcyclobutyl, cyclobutenyl, cyclopentyl, cyclopentenyl, cyclohexyl, cyclohexylcarbonyloxy, cyclohexenyl, cycloheptyl, 2-methylcyclopropyl, cycloheptenyl, 4-methylcyclohexyl, 3-methylcyclopentenyl, 4-(isopropyl)-cyclohexylethyl or 2-methylcyclopropylpentyl, and the like. Examples of heterocyclic radicals are tetrahydrofuranyl, tetrahydrothiofuranyl, thienyl, dioxanyl, pyranyl, furyl, chromenyl, xanthenyl, phenoxathiinyl, oxepane, oxathiolanyl, benzothienyl, and the like.

Examples of substituted and unsubstituted aryl radicals are 4-chlorophenyl, 2,6-dichlorophenyl, 2,5-dichlorophenyl, 3,4-dichlorophenyl, 3-chlorophenyl, 3-bromophenyl, 4-bromoindenyl, 3,4-dibromophenyl, 3,4-dibromonaphthyl, 3-chloro-4-fluorophenyl, 2-fluorophenyl and the like; a mono- or di(hydroxy)aryl radical such as 4-hydroxyphenyl, 3-hydroxyphenyl, 2,4-dihydroxyphenyl, and the like; a nitroaryl group such as 3- or 4-nitrophenyl; a cyanoaryl group, for example, 4-cyanophenyl; a mono- or di(lower alkyl)aryl radical such as 4-methylphenyl, 2,4-dimethylphenyl, 2-methylnaphthyl, 4-(iso-propyl)phenyl, 4-ethylnaphthyl, 3-(n-propyl)phenyl and the like; a mono- or di(alkoxy) aryl radical, for example, 2,6-dimethoxyphenyl, 4-methoxyphenyl, 3-ethoxyindenyl, 4-(iso-propoxy)phenyl, 4-(t-butoxy)phenyl, 3-ethoxy-4-methoxyphenyl and the like; 3- or 4-trifluoromethylphenyl, a mono- or dicarboxyaryl radical such as 4-carboxyphenyl, 4-carboxynaphthyl; a mono- or di(hydroxymethyl)aryl radical such as 3,4-di(hydroxymethyl)phenyl, a mono- or di(aminomethyl) aryl radical such as 2-(aminomethyl)phenyl, or a mono- or di(methylsulfonylamino)aryl radical such as 3-(methylsulfonylamino)naphthyl. For the present process, it is preferred that R1 is methyl, phenyl, or vinyl; however, it is especially preferred that R1 is hydrogen.

In another, more general, embodiment, the invention relates to a process for producing higher molecular weight saturated ketones, the process comprising reacting an aldehyde reactant with a ketone reactant, the ketone reactant having at least one hydrogen atom alpha to the carbonyl, in a reaction mixture comprising the aldehyde reactant, the ketone reactant, and a basic catalyst that may comprise a hydroxide or alkoxide of an alkali- or alkali-earth metal, wherein no more than about 16 wt. % water is provided to the reaction mixture, with respect to the total initial weight of the reaction mixture. The process may be carried out in the presence of a hydrogenation catalyst, which is typically a metal catalyst, wherein the transition metal is typically supported on an inert stable support. The basic aldol catalyst (the hydroxide or alkoxide) may be provided in a solution having a concentration of at least 15 wt. %, or at least 25 wt. %, or at least 50 wt. %, or as a solid. The amount of water in the reaction mixture will, of course, increase during the course of the reaction, because of the water generated by the reaction, and some of this water may optionally be removed during the course of the reaction.

Alternatively, in various embodiments, the amount of water provided to the reaction mixture may be no more than about 12 wt. % water, or no more than about 5 wt. % water, or no more than about 3 wt. % water, or even 1 wt. % water or less, in each case with respect to the total initial weight of the reaction mixture.

In yet a further embodiment, the invention relates to a process for preparing a higher molecular weight saturated ketone compound of the formula:

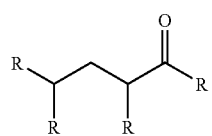

wherein each R is independently a hydrocarbyl group, which process comprises contacting in a reaction mixture an aldehyde compound of the formula

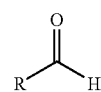

with a ketone compound of the formula

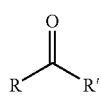

wherein each R is independently a hydrocarbyl group, and R' is a hydrocarbyl group having at least one hydrogen atom on the carbon atom which serves as the point of attachment, in the presence of
(i) an aldol catalyst, comprised of a hydroxide or $C_1$–$C_8$ alkoxide of an alkali metal or alkaline earth metal, wherein the hydroxide or $C_1$–$C_8$ alkoxide of an alkali metal or alkaline earth metal is provided as at least one of:
(a) a solution or
(b) a solid,
wherein no more than about 16 weight percent water is provided to the reaction mixture, with respect to the total weight of the reaction mixture; and
(ii) a heterogeneous hydrogenation catalyst, such as a metal catalyst, wherein the transition metal is typically supported on an inert stable support.

As already noted, in alternative embodiments, the amount of water provided to the reaction mixture may be no more than about 12 weight percent water, or no more than about 5 wt. % water, or no more than about 3 wt. % water, or even 1 wt. % or less, in each case with respect to the total initial weight of the reaction mixture.

Again as noted, when the aldol catalyst is provided as a solution, the solution may have a concentration of at least 15 wt. %, or at least 25 wt. %, or at least 50 wt. %. The aldol catalyst may alternatively be provided as a solid.

As used herein, a "hydrocarbyl" group means a monovalent or divalent, linear, branched, or cyclic group which contains only carbon and hydrogen atoms. Examples of monovalent hydrocarbyls include the following: $C_1$–$C_{20}$ alkyl; $C_1$–$C_{20}$ alkyl substituted with one or more groups selected from $C_1$–$C_{20}$ alkyl, $C_3$–$C_8$ cycloalkyl or aryl; $C_3$–$C_8$ cycloalkyl; $C_3$–$C_8$ cycloalkyl substituted with one or more groups selected from $C_1$–$C_{20}$ alkyl, $C_3$–$C_8$ cycloalkyl or aryl; $C_6$–$C_{14}$ aryl; and $C_6$–$C_{14}$ aryl substituted with one or more groups selected from $C_1$–$C_{20}$ alkyl, $C_3$–$C_8$ cycloalkyl or aryl. As used herein, the term "aryl" preferably denotes a phenyl, napthyl, or anthracenyl group. When the above groups are substituted, they are preferably substituted from one to four times with the listed groups. Examples of divalent (bridging hydrocarbyls) include: —$CH_2$—, —$CH_2CH_2$—, —$C_6H_4$—, and —$CH_2CH_2CH_2$—.

Exemplary aldehydes suitable for use as reactants in the process of the invention include, but are not limited to, acetaldehyde; propionaldehyde; n-butyraldehyde; 2-methyl-propanal; n-pentanal and structural isomers such as 2-methyl-butanal, 3-methyl-butanal, and 2,2-dimethyl-propanal; n-hexanal and structural isomers such as 2-ethyl-butanal, 2,2-dimethylbutanal, 2,3-dimethylbutanal, 2-methyl-pentanal, 3-methylpentanal, and 4-methyl-pentanal; n-heptanal and structural isomers such as 2-methylhexanal, 2-ethylpentanal, 2,2-dimethylpentanal, 2,3-dimethylpentanal, 2,4-dimethylpentanal, 2-ethyl-3-methylbutanal, and 2-ethyl-2-methylbutanal; n-octanal and structural isomers such as 2-ethylhexanal, n-nonanal and structural isomers; n-decanal and structural isomers; n-undecanal and structural isomers; n-dodecanal and structural isomers; benzaldehyde; 4-chlorobenzaldehyde; 3-chlorobenzaldehyde; 2-chlorobenzaldehyde; phenyl acetaldehyde; o-tolualdehyde; m-tolualdehyde; p-tolualdehyde; p-methoxybenzaldehyde; o-methoxybenzaldehyde; m-methoxybenzaldehyde; cyclopropane carboxaldehyde; cyclobutane carboxaldehyde; cyclopentane carboxaldehyde; cyclohexane carboxaldehyde; 2-methylcyclohexane carboxaldehyde; 3-methylhexane carboxaldehyde; 4-methylhexane carboxaldehyde.

Exemplary ketones suitable for use as reactants in the process of the invention include, but are not limited to, acetone, 2-butanone, 2-pentanone, 3-methyl-2-butanone, 2-hexanone, 4-methyl-2-pentanone, 3-methyl-2-pentanone, pinacolone, 2-heptanone, 5-methyl-2-hexanone, 2-octanone, 2-nonanone, 2-decanone, 2-undecanone, 2-dodecanone, cyclobutanone, cyclopentanone, cyclohexanone, acetophenone. Preferred ketones are methyl ketones.

As further described below, the parameters that affect yield, space-time yield, and selectivity include the temperature chosen, the amount and concentration of aldol catalyst, the amount of water present in the reaction mixture, the ratio of aldol catalyst to aldehyde, the ratio of ketone to aldehyde, and the residence time.

The reactants may be either liquids or solids at room temperature. It is preferred that there be low levels, generally less than 1–2%, of the corresponding acid derived from the aldehyde reactant. This acid, if present, tends to neutralize the small amount of base used as catalyst. Thus, one may need to add sufficient caustic to neutralize any acid present, and then provide a caustic/aldehyde ratio within the specifications of the invention (above that of the acid present). Feeds with higher levels of acid may be used, but result in expensive and unnecessarily high catalyst usage. For example, if n-butyraldehyde contaminated with 5 wt % n-butyric acid were condensed with acetone using 0.01 equivalents of 50% caustic catalyst per mole of n-butyraldehyde, according to the invention, then an additional 0.04 equivalents of caustic per mole of butyraldehyde would be added to the feed to neutralize the butyric acid. Thus, the catalyst usage is 5 times higher when the acid contaminant is present in the feed at the 5 wt % level.

According to the invention, the molar ratio of ketone and aldehyde concentration in the reaction zone can be varied over a wide range. To avoid the separation and recycle of unnecessarily large amounts of ketone, in general 1 to 20 moles of ketone may be used per mole of aldehyde, or from 1 to 14 moles of ketone per mole of aldehyde, or from 1.05 to 10 moles per mole.

Liquid bases provided as the aldol catalyst, that are suitable for use as catalysts for the aldol condensation reaction and the dehydration reaction, include solutions of the hydroxides or alkoxides of alkali-metals or alkaline-earth metals. These aldol catalysts include, but are not limited to, sodium hydroxide, potassium hydroxide, cesium hydroxide, lithium hydroxide, magnesium hydroxide, calcium hydroxide, barium hydroxide, sodium methoxide, sodium ethoxide, sodium propoxide, sodium butoxide, potassium methoxide, potassium ethoxide, potassium propoxide, potassium butoxide, cesium methoxide, cesium ethoxide, cesium propoxide, cesium butoxide, lithium methoxide, lithium ethoxide, lithium propoxide, lithium butoxide, magnesium methoxide, magnesium ethoxide, magnesium propoxide, magnesium butoxide, calcium methoxide, calcium ethoxide, calcium propoxide, calcium butoxide, barium methoxide, barium ethoxide, barium propoxide, barium butoxide. Sodium hydroxide or potassium hydroxide may be preferred because they are readily available and inexpensive.

The amount of the aldol catalyst (base) to be added can vary within wide limits. However, it has been found that from 0.001 to 0.45 equivalents, or from 0.005 to 0.15 equivalents of base, or from 0.005 to 0.10 equivalents, relative to the molar amount of aldehyde, are sufficient and thus help to avoid an unnecessarily high consumption of base, as well as to avoid formation of a separate and distinct catalyst-containing phase. The base can be added to the reaction mixture either as such or in dissolved form. It may be most convenient to provide the base in dissolved form.

The concentration of catalyst, or base, useful according to the invention can likewise vary, although higher concentrations than are typically used in the art are a feature of the claimed invention. According to the invention, the catalyst may be provided as an aqueous solution, with a concentration of at least about 15 wt. %, or at least 20 wt. %, or at least 25 wt. %, and even at 50 wt. % or more, although the catalyst can be provided as a 100 wt. % solid. Particularly satisfactory results are obtained with a catalyst concentration of 25 wt. % or above. We have found that the concentration of the aqueous solution used, perhaps by adding to the total amount of water present in the reaction mixture, can affect the yield and selectivity for the target product, and that relatively small amounts of a higher concentration catalyst are much preferred.

In one embodiment, the amount of water provided to the reaction mixture, or reaction zone, is no more than about 16 wt. %, with respect to the total initial weight of the reaction mixture. In other embodiments, the amount of water provided to the reaction mixture, or reaction zone, is no more than about 12 wt. %, with respect to the total weight of the reaction mixture, or no more than about 5 wt. %, or no more than 3 wt. %, or even 1 wt. % or less.

In this regard, it is significant according to the invention that the total amount of water present throughout the reaction zone, with respect to the total weight of the reaction mixture, be limited. This may be achieved according to the invention by limiting the amount of water provided to the reaction mixture, as already noted. In this aspect, the total amount of water present may include the water present in the reaction mixture initially, as well as the water of reaction created during the course of the reaction, minus any water removed during the reaction, for example via distillation. Not being bound by any theory, we believe that limiting the amount of water present in the reaction mixture, with respect to the total weight of reactants, may alter the solvating environment around the alkali or alkaline earth metal catalyst which favors an enhancement of the cross-aldol, versus self-aldol, condensation ratio. This enhancement may be due to the preferred coordination of the alkali or alkaline earth metal catalyst to the carbonyl of a reactive ketone or aldehyde.

The processes according to the invention may be carried out in the substantial absence of any compatibilizing agents, solubilizing agents, or phase transfer agents. "Substantial absence" means that these agents are not added to the reaction mixture as such, nor are they intentionally generated in situ. While one or more of these agents may inadvertently be generated during reaction, they are nonetheless not present in the reaction mixture in appreciable amounts.

Categories of these compatibilizing agents or phase transfer agents include, but are not limited to, alkanols, polyols, and polyether alcohols, and other compounds known in the art to act as surfactants, such as carboxylic acid salts, sulfonates, ethoxylates, amines, and amides. These agents are generally characterized by their ability to reduce the interfacial tension of normally immiscible liquids. Examples of such agents include, but are not limited to, carboxylic acid salts of the corresponding reactant aldehyde; alkanols containing one to 6 carbon atoms, such as methanol, ethanol, propanol, isopropanol, butanol, isobutanol, pentanol and its C-5 analogs, and hexanol and its C-6 analogs; glycerol or another sugar alcohol; ethylene glycol; diethylene glycol; propylene glycol; dipropylene glycol; 1,3-propanediol; 1,2-propanediol; butylene glycols; erythritol and isomeric tetrahydric alcohols; pentaerythritol; various pentahydric alcohols such as arabitol and xylitol; hexahydric alcohols; polyhydric alcohols not derived from sugar alcohols, such as inositol, and related compounds, isomers, and homologs; salts of aromatic sulfonic acids; polyethylene glycol; polypropylene glycol; diglyme, triglyme, and tetraglyme. By not adding these compatibilizing or phase transfer agents to the reaction mixture, subsequent separation steps are thereby avoided.

Solubilizing agents may nonetheless be introduced into the reaction zone, such as if an alkanol solution of an alkali metal or alkaline earth metal alkoxide is used as the catalyst. For example, sodium methoxide is available in commercial quantities as a 50 wt % solution in methanol. If the catalyst-to-aldehyde ratio is kept within the scope of the invention while using such an alkoxide catalyst, then the alcohol in which the alkoxide is provided is not present in sufficient quantities to act as a solubilizing agent according to the practice in the prior art (see, for example, U.S. Pat. Nos. 2,088,015 ('015), 2,0880,016 ('016), 2,0880,017 ('017), and 2,088,018 ('018). If these solubilizing agents are introduced into the reaction zone as part of the catalyst feed, the amount is preferably no more than 8 wt. %, based on the total weight of reactants, or no more than 5 wt. %, or no more than 2 wt. %, or 1 wt. %, or less.

The solid hydrogenation catalysts useful according to the invention may be metal catalysts, wherein the transition metal is typically supported on an inert stable support. Preferred hydrogenation catalysts include, but are not limited to, transition metal catalyst systems having active components comprised of Ni, Co, Cu, or Cr; noble metal catalyst systems having active components comprised of Pt, Pd, Rh, Ru, Re, or Ir; and combinations of these catalysts. Suitable supports include, but are not limited to, alumina, silica, a combination of alumina and silica, denoted as silica-alumina, and carbon. Pd on C is a preferred solid hydrogenation catalyst.

The metal weight loadings of the solid hydrogenation catalysts useful according to the invention may vary within a wide range, from about 0.1 to about 90 wt. %, or even greater. It is generally understood that catalytic activity is controlled by the exposed transition metal surface area of such catalysts. Therefore, the desired weight loadings of catalysts in this process will be governed by the activity desired in the hydrogenation process. A typical metal weight loading may be from about 0.1 to about 5.0 wt. %.

The reactor temperature can be chosen, in general, within a wide range, for example from about 0° C. to about 200° C. Lower temperatures result in incomplete conversions and often require longer residence times in the reactor, which result in the production of unwanted high boiling impurities. Higher temperatures, which yield higher conversions, also result in unwanted high boiling impurities, and increase the probability for over-hydrogenation. In other embodiments, the reaction temperature may be from about 25° C. to about 175° C., or from 50° C. to 165° C., or from 90° to 130° C.

The reaction pressure of the hydrogen gas provided in the reactor, chosen to optimize conversion and selectivity, is generally from about 3 to about 150 bar. Sufficient hydrogenation of the olefinic group of the unsaturated ketone intermediate should be balanced against over-hydrogenation of the carbonyl group to an alcohol. In various embodiments, the pressure may also be from about 6 to about 200 bar, or from about 10 to about 70 bar, or from about 15 to about 50 bar.

Residence time is the average length of time the reactants spend in the reactor. Thus the residence time is the amount of material in the reactor (the volume of the reactor), divided by either the inflow or the outflow, which are equal when the system is at equilibrium. A relatively wide range of residence times can be employed according to the invention, such as from about 2 to about 200 minutes. The suitable residence time, while chosen to optimize both conversion and selectivity, will be related to the composition of the hydrogenation catalyst and its loading in the reaction zone, the ratio of aldehyde to ketone fed to the reaction zone, the amount and concentration of basic catalyst, the temperature, and the pressure. Thus, the residence time may be from about 2 to about 200 minutes, or from about 2 to about 100 minutes, or from about 5 to about 70 minutes.

This invention can be further illustrated by the following examples of preferred embodiments thereof, although it will be understood that these examples are included merely for purposes of illustration and are not intended to limit the scope of the invention unless otherwise specifically indicated.

EXPERIMENTAL

For the examples and comparative examples described herein, unless otherwise noted, conversion and selectivity terms are defined as follows:

$$\% \text{ Conversion of n-butyraldehyde} = \frac{\text{moles n-butyraldehyde reacted}}{\text{moles n-butyraldehyde in feed}}$$

$$\% \text{ Selectivity} = \frac{\text{moles Methyl Amyl Ketone formed}}{\text{moles n-butyraldehyde reacted}}$$

$$\text{Space-Time Yield} = \frac{\text{Methyl Amyl Ketone formed per unit time [lbs/hour]}}{\text{Reactor volume [ft3]}}$$

Unless otherwise indicated, all analyses were done by gas chromatography using a Hewlett-Packard model 5890 gas chromatograph, equipped with a DB-5 column, TC detector, and auto injector. For each analysis, the initial temperature of the column was set at 35° C., held for 2 minutes, and ramped to 250° C. at a rate of 20° C. per minute, and held for 2 to 5 minutes at 250° C.

EXAMPLES

Example 1 (Comparative)

Batch Slurry Production of Methyl Amyl Ketone With Dilute Caustic 70.25 grams of acetone, 26.84 grams of n-butyraldehyde, 1.35 grams of 1% Pd/C catalyst (Engelhard CG-31, available from Engelhard Corporation, Iselin, N.J.), and 45 mL of 3-wt % sodium hydroxide were charged to a 300 ml autoclave fitted with a magnetic stirrer, nitrogen purge, cooling coil, and temperature-controlled heater. The concentration of water initially in the reactor was 31.4 weight percent, with a caustic to n-butyraldehyde molar feed ratio of 0.093. The autoclave was sealed, purged with nitrogen, pressurized to 20 bar of hydrogen, and heated to 100° C. After stirring the mixture for 1 hour at 100° C., the solution was cooled and the pressure was released. The reaction mixture separated into two liquid phases. The product samples were analyzed, as were all the samples of the application, by capillary GLC analysis. The aqueous phase contained water, caustic, acetone, and minor amounts of other components. Composition of the organic phase and a summary of other results are given in Table 1.

Example 2 (Comparative)

Continuous Slurry Production of Methyl Amyl Ketone With Dilute Caustic

The experiment was carried out in a continuous mode of operation utilizing a 1 L autoclave, with 500 mL of working volume. 12 grams of a 1% Pd/C catalyst (Engelhard CG-31) was loaded into the autoclave. An in-line filter was attached to prevent catalyst loss. A 2.5-wt % sodium hydroxide solution was pumped into the autoclave at a rate of 4.25 mL/min. An organic solution, a mixture of acetone and n-butyraldehyde (3.2:1 molar ratio), was pumped into the system at 6 mL/min. This gave a residence of approximately 49 minutes. The combined feed streams comprised 50 weight percent water, with a caustic to n-butyraldehyde molar feed ratio of 0.17. The system was pressurized with 300 psig of hydrogen and heated to 100° C. The system was allowed to reach steady state operation at the correct process settings (temperature, pressure, and feed rate), and run for an additional 3 hours at steady state before sampling. The product samples separated into two liquid phases and were analyzed by capillary GLC. The aqueous phase contained water, caustic, acetone and minor amounts of other components. Composition of the organic phase and a summary of other results are given in Table 1.

TABLE 1

Results from Examples 1 and 2 (Comparative)

| MAK Product Composition With Dilute Caustic | Example 1 Batch Slurry | Example 2 Continuous Slurry |
|---|---|---|
| Acetone | 26.9 | 21.64 |
| n-butyraldehyde | 0.03 | 0.31 |
| Methyl Isobutyl Ketone | 3.22 | 2.07 |
| Methyl Amyl Ketone | 28.2 | 55.56 |
| 3-heptene-2-one | 0.008 | 3.5 |
| 2-ethyl-hexaldehyde | 1.1 | 0.291 |
| High and low boilers | 27.71 | 10.77 |
| n-butyraldehyde conversion, % | 99.93 | 99.32 |
| Selectivity, % | 41.09 | 75.52 |
| Space-Time Yield, lb/ft$^3$-hr | 5.9 | 10.4 |

Example 3 (Inventive)

The experiment was carried out in a continuous mode of operation utilizing a 1 L autoclave, with 500 mL of working volume. 20 grams of a 1% Pd/C catalyst (Engelhard CG-31) was loaded into the autoclave. An in-line filter was attached to prevent catalyst loss. A 50-wt % sodium hydroxide solution was pumped into the autoclave at a rate of 0.065 mL/min. An organic solution, a mixture of acetone and n-butyraldehyde (10:1 molar ratio), was pumped into the system at 49.93 mL/min. This gave a residence time of approximately 10 minutes. The combined feed streams comprised 0.14 weight percent water, with a caustic to n-butyraldehyde molar feed ratio of 0.024. The system was pressurized with 300 psig of hydrogen and heated to 105° C. The system was allowed to reach steady state operation at the correct process settings (temperature, pressure, and feed rate), and run for an additional 3 hours at steady state before sampling. The product samples were analyzed by capillary GLC to determine percent conversion of n-butyraldehyde, selectivity to 2-heptanone (MAK), and space-time yield of MAK. A summary of results is given in Table 2. Water content of the reactor effluent was about 5 weight percent.

Example 4 (Inventive)

The experiment was carried out in a continuous mode of operation utilizing a 1 L autoclave, with 500 mL of working volume. 20 grams of a 1% Pd/C catalyst (Engelhard CG-31) was loaded into the autoclave. An in-line filter was attached to prevent catalyst loss. A 25-wt % sodium hydroxide solution was pumped into the autoclave at a rate of 0.266 mL/min. An organic solution, a mixture of acetone and n-butyraldehyde (2:1 molar ratio), was pumped into the system at 8.06 mL/min. This gave a residence of approximately 60 minutes. The combined feed streams comprised 4.4 weight percent water, with a caustic to n-butyraldehyde molar feed ratio of 0.074. The system was pressurized with 300 psig of hydrogen and heated to 120° C. The system was allowed to reach steady state operation at the correct process settings (temperature, pressure, and feed rate), and run for an additional 3 hours at steady state before sampling. The product samples were analyzed by capillary GLC to determine percent conversion of n-butyraldehyde, selectivity to 2-heptanone (MAK), and space-time yield of MAK. A summary of results is given in Table 2. Water content of the reactor effluent was about 12 weight percent.

Example 5 (Inventive)

The experiment was carried out in a continuous mode of operation utilizing a 1 L autoclave, with 500 mL of working volume. 20 grams of a 1% Pd/C catalyst (Engelhard CG-31) was loaded into the autoclave. An in-line filter was attached to prevent catalyst loss. A 37.5-wt % sodium hydroxide solution was pumped into the autoclave at a rate of 0.173 mL/min. An organic solution, a mixture of acetone and n-butyraldehyde (6:1 molar ratio), was pumped into the system at 14.13 mL/min. This gave a residence of approximately 35 minutes. The combined feed streams comprised 1.5 weight percent water, with a caustic to n-butyraldehyde molar ratio of 0.099. The system was pressurized with 300 psig of hydrogen and heated to 100° C. The system was allowed to reach steady state operation at the correct process settings (temperature, pressure, and feed rate), and run for an additional 3 hours at steady state before sampling. The product samples were analyzed by capillary GLC to determine percent conversion of n-butyraldehyde, selectivity to 2-heptanone (MAK), and space-time yield of MAK. A summary of results is given in Table 2. Water content of the reactor effluent was about 6.5 weight percent.

TABLE 2

Results from Examples 3, 4, and 5 (Inventive)

| MAK Product Composition, weight % | Example 3 | Example 4 | Example 5 |
|---|---|---|---|
| Acetone | 57.33 | 35.94 | 47.87 |
| n-butyraldehyde | 0.36 | 0.00 | 0.10 |
| Methyl Isobutyl Ketone | 3.99 | 7.59 | 6.12 |
| Methyl Amyl Ketone | 24.96 | 38.56 | 26.00 |
| 3-heptene-2-one | 0.55 | 0.00 | 0.18 |
| 2-ethyl-hexaldehyde | 0.00 | 0.00 | 0.00 |
| High and low boilers | 1.55 | 4.94 | 3.34 |
| n-butyraldehyde conversion | 97.95 | 100.00 | 99.4 |
| Selectivity | 88.43 | 85.05 | 85.13 |
| Space-Time Yield, lb/ft$^3$-hr | 39.0 | 21.0 | 16.9 |

Examples 6–20 (Inventive)

Examples 6–20 were carried out in a continuous mode of operation utilizing a 1 L autoclave, with 500 mL of working volume. For each experiment, 20 grams of a 1% Pd/C catalyst (Engelhard CG-31) was loaded into the autoclave. An in-line filter was attached to prevent catalyst loss. Sodium hydroxide solution and a mixture of acetone and n-butyraldehyde were pumped into the autoclave continuously. The system was pressurized with 300 psig of hydrogen and heated to the designated temperature. Feed conditions are summarized in Table 3. The system was allowed to reach steady state operation at the correct process settings (temperature, pressure, and feed rate), and run for an additional 3 hours at steady state before sampling. The product samples were analyzed by capillary GLC to determine percent conversion of n-butyraldehyde, selectivity to 2-heptanone (MAK), and space-time yield of MAK. A summary of results is given in Table 4.

TABLE 3

Feed Conditions for Examples 6–20

| | Example 6 | Example 7 | Example 8 | Example 9 | Example 10 | Example 11 | Example 12 | Example 13 | Example 14 |
|---|---|---|---|---|---|---|---|---|---|
| Temperature, Celsius | 75 | 100 | 100 | 100 | 100 | 100 | 100 | 100 | 125 |
| Caustic Concentration, wt % | 50 | 37.5 | 37.5 | 37.5 | 37.5 | 37.5 | 37.5 | 37.5 | 50 |
| Ketone: Aldehyde Molar Ratio | 10 | 6 | 6 | 6 | 6 | 6 | 10 | 6 | 2 |
| Organic Flow, ml/min | 42.99 | 14.13 | 13.8 | 14.1 | 14.3 | 8.2 | 13.9 | 14.1 | 47.1 |
| Caustic Flow, ml/min | 7.01 | 0.173 | 0.52 | 0.17 | 0.04 | 0.10 | 0.40 | 0.17 | 1.91 |
| Residence Time, minutes | 9 | 31 | 31 | 31 | 31 | 53 | 31 | 31 | 9 |
| Water in Feed, wt % | 12.00% | 1.34% | 3.93% | 1.34% | 0.33% | 1.34% | 3.08% | 1.34% | 3.63% |

| | Example 15 | Example 16 | Example 17 | Example 18 | Example 19 | Example 20 |
|---|---|---|---|---|---|---|
| Temperature, Celsius | 125 | 125 | 125 | 125 | 125 | 115 |
| Caustic Concentration, wt % | 50 | 25 | 25 | 25 | 50 | 25 |
| Ketone: Aldehyde Molar Ratio | 10 | 10 | 2 | 10 | 2 | 6 |
| Organic Flow, ml/min | 49.9 | 8.3 | 7.2 | 48.1 | 8.3 | 14.1 |
| Caustic Flow, ml/min | 0.07 | 0.03 | 1.17 | 1.96 | 0.04 | 0.17 |
| Residence Time, minutes | 8 | 50 | 52 | 8 | 51 | 30 |
| Water in Feed, wt % | 0.13% | 0.38% | 15.61% | 4.64% | 0.46% | 1.46% |

TABLE 4

Results for Examples 6–20

| | Example 6 | Example 7 | Example 8 | Example 9 | Example 10 | Example 11 | Example 12 | Example 13 | Example 14 |
|---|---|---|---|---|---|---|---|---|---|
| Acetone | 69.39 | 58.10 | 54.15 | 43.77 | 41.67 | 49.54 | 64.39 | 57.17 | 31.72 |
| n-butyraldehyde | 1.92 | 1.10 | 0.45 | 0.16 | 0.32 | 0.10 | 0.16 | 0.30 | 1.00 |
| Methyl Isobutyl Ketone | 0.51 | 1.60 | 3.78 | 8.16 | 7.52 | 7.32 | 1.48 | 3.67 | 0.59 |
| Methyl Amyl Ketone | 14.23 | 23.29 | 24.93 | 32.21 | 35.31 | 29.56 | 17.08 | 27.15 | 35.02 |
| 3-hepten-2-one | 1.45 | 1.39 | 0.66 | 0.26 | 0.37 | 0.19 | 0.16 | 0.39 | 4.07 |
| 2-ethyl-hexaldehyde | 0.05 | 0.03 | 0.02 | 0.01 | 0.01 | 0.00 | 0.01 | 0.01 | 0.11 |
| High and Low Boilers | 3.23 | 7.26 | 8.87 | 5.09 | 6.44 | 4.58 | 4.40 | 4.50 | 21.79 |
| n-butyraldehyde Conversion | 87.13 | 95.10 | 98.06 | 99.35 | 98.84 | 99.57 | 98.93 | 98.59 | 97.63 |
| Selectivity | 59.83 | 65.08 | 67.25 | 82.83 | 80.41 | 83.59 | 74.16 | 81.35 | 52.23 |
| Space-Time Yield, lb/ft$^3$-hr | 21.33 | 12.37 | 12.85 | 16.44 | 16.03 | 9.69 | 9.27 | 16.02 | 72.71 |
| Outlet Water Concentration, wt % | 15.35% | 7.11% | 10.28% | 8.64% | 8.26% | 8.25% | 7.03% | 6.66% | 14.19% |

TABLE 4-continued

Results for Examples 6–20

| | Example | | | | | |
|---|---|---|---|---|---|---|
| | 15 | 16 | 17 | 18 | 19 | 20 |
| Acetone | 63.49 | 37.78 | 24.37 | 70.12 | 27.26 | 34.63 |
| n-butyraldehyde | 0.14 | 0.02 | 0.03 | 0.29 | 0.02 | 0.02 |
| Methyl Isobutyl Ketone | 5.74 | 26.77 | 17.82 | 1.45 | 14.42 | 14.73 |
| Methyl Amyl Ketone | 16.47 | 17.84 | 38.08 | 11.16 | 37.11 | 31.01 |
| 3-hepten-2-one | 0.29 | 0.02 | 0.06 | 1.18 | 0.07 | 0.10 |
| 2-ethyl-hexaldehyde | 0.00 | 0.00 | 0.02 | 0.00 | 0.00 | 0.00 |
| High and Low Boilers | 2.55 | 2.93 | 6.97 | 8.87 | 8.45 | 4.59 |
| n-butyraldehyde Conversion | 98.93 | 99.88 | 99.89 | 98.01 | 99.93 | 99.92 |
| Selectivity | 81.99 | 83.04 | 80.29 | 48.44 | 78.32 | 83.39 |
| Space-Time Yield, lb/ft^3-hr | 34.96 | 5.94 | 17.40 | 19.71 | 19.65 | 16.16 |
| Outlet Water Concentration, wt % | 4.53% | 8.73% | 26.11% | 8.46% | 10.36% | 10.11% |

The invention has been described in detail with particular reference to preferred embodiments, but it will be understood that variations and modifications can be effected within the spirit and scope of the invention. In the specification, there have been disclosed typical preferred embodiments of the invention and, although specific terms are employed, they are used in a generic and descriptive sense only, and not for purposes of limitation, the scope of the invention being set forth in the following claims.

We claim:

1. A process for producing a higher molecular weight saturated ketone, the process comprising reacting an aldehyde reactant with a ketone reactant having at least one hydrogen atom alpha to the carbonyl, in a reaction mixture comprising the aldehyde reactant, the ketone reactant, and an aldol catalyst comprised of a hydroxide or alkoxide of an alkali metal or an alkaline earth metal provided as a solution or as a solid,
wherein no more than about 16 wt. % water is provided to the reaction mixture, with respect to the total initial weight of the reaction mixture, the molar ratio of ketone reactant to aldehyde reactant is from 1:1 to 20:1, and the molar ratio of the hydroxide or alkoxide of the alkali metal or alkaline earth metal aldol catalyst to the aldehyde reactant is from 0.001:1 to 0.45:1, and
wherein the reacting is carried out at a reaction time of no more than 120 minutes in a reactor provided with a solid hydrogenation catalyst and hydrogen gas.

2. The process according to claim 1, wherein no more than 12 wt. % water is provided to the reaction mixture, with respect to the total initial weight of the reaction mixture.

3. The process according to claim 1, wherein no more than 5 wt. % water is provided to the reaction mixture, with respect to the total initial weight of the reaction mixture.

4. The process according to claim 1, wherein no more than 3 wt. % water is provided to the reaction mixture, with respect to the total initial weight of the reaction mixture.

5. The process according to claim 1, wherein no more than 1 wt. % water is provided to the reaction mixture, with respect to the total initial weight of the reaction mixture.

6. The process according to claim 1, wherein the aldol catalyst is provided as a solution of a hydroxide or alkoxide of an alkali metal or an alkaline earth metal, wherein the hydroxide or alkoxide is provided in the solution at a concentration of at least 15 wt. %.

7. The process according to claim 1, wherein the aldol catalyst is provided as a solution of a hydroxide or alkoxide of an alkali metal or an alkaline earth metal, wherein the hydroxide or alkoxide is provided in the solution at a concentration of at least 25 wt. %.

8. The process according to claim 1, wherein the aldol catalyst is provided as a solution of a hydroxide or alkoxide of an alkali metal or an alkaline earth metal, wherein the hydroxide or alkoxide is provided in the solution at a concentration of at least 50 wt. %.

9. The process according to claim 1, wherein the reacting is carried out in the substantial absence of a solubilizing agent.

10. The process according to claim 1, wherein the molar ratio of ketone reactant to aldehyde reactant is from 1:1 to 14:1.

11. The process according to claim 1, wherein the molar ratio of ketone reactant to aldehyde reactant is from 1.05 to 10.

12. The process according to claim 1, wherein the molar ratio of the hydroxide or alkoxide of an alkali metal or alkaline earth metal aldol catalyst to the aldehyde reactant is from 0.005:1 to 0.45:1.

13. The process according to claim 1, wherein the molar ratio of the hydroxide or alkoxide of the alkali metal or alkaline earth metal aldol catalyst to the aldehyde reactant is from 0.001:1 to 0.25:1.

14. The process according to claim 1, wherein the molar ratio of the hydroxide or alkoxide of the alkali metal or alkaline earth metal aldol catalyst to the aldehyde reactant is from 0.005:1 to 0.15:1.

15. The process according to claim 1, wherein the molar ratio of the hydroxide or alkoxide of the alkali metal or alkaline earth metal aldol catalyst to the aldehyde reactant is from 0.005:1 to 0.10:1.

16. The process according to claim 1, wherein the hydroxide or alkoxide of the alkali metal or alkaline earth metal comprises one or more of: sodium hydroxide, potassium hydroxide, cesium hydroxide, lithium hydroxide, magnesium hydroxide, calcium hydroxide, barium hydroxide, sodium methoxide, sodium ethoxide, sodium propoxide, sodium butoxide, potassium methoxide, potassium ethoxide, potassium propoxide, potassium butoxide, cesium methoxide, cesium ethoxide, cesium propoxide, cesium butoxide, lithium methoxide, lithium ethoxide, lithium propoxide, lithium butoxide, magnesium methoxide, magnesium ethoxide, magnesium propoxide, magnesium butoxide, calcium methoxide, calcium ethoxide, calcium propoxide, calcium butoxide, barium methoxide, barium ethoxide, barium propoxide, or barium butoxide.

17. The process according to claim 1, wherein the hydroxide or alkoxide of the alkali metal or alkaline earth metal comprises one or more of: sodium hydroxide or potassium hydroxide.

18. The process according to claim 1, wherein the reacting is carried out at a temperature from 25° C. to 200° C.

19. The process according to claim 1, wherein the reacting is carried out at a temperature from 40° C. to 175° C.

20. The process according to claim 1, wherein the aldol catalyst is provided as an oxide of an alkali metal or an alkaline earth metal which forms in the reaction mixture a hydroxide.

21. The process according to claim 1, wherein the reacting is carried out in a series of two or more continuous stirred tank reactors.

22. The process according to claim 1, wherein the aldehyde reactant comprises one or more of: acetaldehyde; propionaldehyde; n-butyraldehyde; 2-methyl-propanal; n-pentanal; 2-methyl-butanal; 3-methyl-butanal; 2,2-dimethyl-propanal; n-hexanal; 2-ethyl-butanal; 2,2-dimethylbutanal; 2,3-dimethylbutanal; 2-methyl-pentanal; 3-methyl-pentanal; 4-methyl-pentanal; n-heptanal; 2-methylhexanal; 2-ethylpentanal; 2,2-dimethylpentanal; 2,3-dimethylpentanal; 2,4-dimethylpentanal; 2-ethyl-3-methylbutanal; 2-ethyl-2-methylbutanal; n-octanal; 2-ethylhexanal; n-nonanal; n-decanal; n-undecanal; n-dodecanal; benzaldehyde; 4-chlorobenzaldehyde; 3-chlorobenzaldehyde; 2-chlorobenzaldehyde; phenyl acetaldehyde; o-tolualdehyde; m-tolualdehyde; p-tolualdehyde; p-methoxybenzaldehyde; o-ethoxybenzaldehyde; m-methoxybenzaldehyde; cyclopropane carboxaldehyde; cyclobutane carboxaldehyde; cyclopentane carboxaldehyde; cyclohexane carboxaldehyde; 2-methylcyclohexane carboxaldehyde; 3-methylhexane carboxaldehyde; or 4-methylhexane carboxaldehyde.

23. The process according to claim 1, wherein the ketone reactant comprises one or more of: acetone, 2-butanone, 2-pentanone, 3-methyl-2-butanone, 2-hexanone, 4-methyl-2-pentanone, pinacolone, 2-heptanone, 5-methyl-2-hexanone, 2-octanone, 2-nonanone, 2-decanone, 2-undecanone, 2-dodecanone, cyclobutanone, cyclopentanone, cyclohexanone, cyclooctanone, 3,3-5-trimethylcyclohexanone, tricyclo[5.2.1.02,6]decan-8-one, or acetophenone.

24. The process according to claim 1, wherein the hydrogen gas is provided at a pressure from about 3 to about 150 bar.

25. The process according to claim 1, wherein the hydrogen gas is provided at a pressure from about 15 to about 50 bar.

26. The process according to claim 1, wherein the residence time of the reaction mixture in the reactor is from about 2 to about 200 minutes.

27. The process according to claim 1, wherein the residence time of the reaction mixture in the reactor is from about 5 to about 60 minutes.

28. The process according to claim 1, where the hydrogenation catalyst is a shaped or extruded transition metal catalyst supported on a stable support.

29. The process according to claim 1, wherein the hydrogenation catalyst comprises one or more of: Ni, Co, Cu, Cr, Pt, Pd, Rh, Ru, Re, or Ir.

30. The process according to claim 1, wherein the hydrogenation catalyst is supported on a support comprising one or more of: alumina, silica, silica-alumina, or carbon.

31. The process according to claim 1, wherein the hydrogenation catalyst comprises palladium on carbon.

32. The process according to claim 1, wherein the hydrogenation catalyst has a metal loading of from about 0.1 to about 90 wt. %.

33. The process according to claim 1, wherein the hydrogenation catalyst has a metal loading of from about 0.1 to about 5 wt. %.

34. A process for producing 2-heptanone, the process comprising reacting n-butyraldehyde with acetone, in a reaction mixture comprising the n-butyraldehyde, the acetone, and an aldol catalyst comprised of a hydroxide or alkoxide of an alkali metal or an alkaline earth metal provided as a solution or as a solid, wherein no more than about 16 wt. % water is provided to the reaction mixture, with respect to the total initial weight of the reaction mixture, the molar ratio of acetone reactant to n-butyraldehyde reactant is from 1:1 to 20:1, and the molar ratio of the hydroxide or alkoxide of the alkali metal or alkaline earth metal aldol catalyst to the butyraldehyde reactant is from 0.001:1 to 0.45:1, and wherein the reacting is carried out at a reaction time of no more than 120 minutes in a reactor provided with a solid hydrogenation catalyst and hydrogen gas.

* * * * *

UNITED STATES PATENT AND TRADEMARK OFFICE
CERTIFICATE OF CORRECTION

PATENT NO.        : 7,071,361 B2
APPLICATION NO. : 10/877339
DATED             : July 4, 2006
INVENTOR(S)      : Barnicki et al.

It is certified that error appears in the above-identified patent and that said Letters Patent is hereby corrected as shown below:

Page 1, Assignee Information "Fastman" should read --Eastman--.

Signed and Sealed this

Third Day of October, 2006

JON W. DUDAS
*Director of the United States Patent and Trademark Office*